(12) United States Patent
Damadian et al.

(10) Patent No.: US 11,141,080 B1
(45) Date of Patent: Oct. 12, 2021

(54) CERVICAL VERTEBRA ANGLE MEASUREMENT

(71) Applicant: Fonar Corporation, Melville, NY (US)

(72) Inventors: Raymond V. Damadian, Woodbury, NY (US); Robert Wolf, Medford, NY (US)

(73) Assignee: Fonar Corporation, Melville, NY (US)

( * ) Notice: Subject to any disclaimer, the term of this patent is extended or adjusted under 35 U.S.C. 154(b) by 0 days.

(21) Appl. No.: 14/208,343

(22) Filed: Mar. 13, 2014

Related U.S. Application Data

(60) Provisional application No. 61/779,165, filed on Mar. 13, 2013, provisional application No. 61/779,388, filed on Mar. 13, 2013.

(51) Int. Cl.
*A61B 5/11* (2006.01)
*A61B 5/055* (2006.01)
*A61B 5/00* (2006.01)

(52) U.S. Cl.
CPC ............ *A61B 5/1128* (2013.01); *A61B 5/055* (2013.01); *A61B 5/4566* (2013.01)

(58) Field of Classification Search
CPC .......... H05G 1/64; A61B 6/505; A61B 6/055; A61B 6/5217; A61B 6/5223; G01R 33/00;

(Continued)

(56) References Cited

U.S. PATENT DOCUMENTS 3,810,254 A 5/1974 Utsumi et al.
4,407,292 A 10/1983 Edrich et al.
(Continued)

FOREIGN PATENT DOCUMENTS

DE 3140225 A1 4/1983
JP 1242056 9/1989
(Continued)

OTHER PUBLICATIONS

Duan et al. Three-dimensional CT study on normal anatomical features of atlanto-axial joints. 2007 Surg. Radiol. Anat. 29:83-88.*
(Continued)

*Primary Examiner* — Michael J Tsai
*Assistant Examiner* — Patrick M Mehl
(74) *Attorney, Agent, or Firm* — Lerner, David, Littenberg, Krumholz & Mentlik, LLP

(57) ABSTRACT

This disclosure provides a method of measuring the axial rotation of a selected vertebra of a patient using a magnetic resonance (MR) image. The method includes: identifying, in the MR image, two or more features of the selected vertebra; determining a first axis connecting the identified features; identifying, in the MR image, two or more features of the patient's surrounding anatomy that are not features of the selected vertebra; determining a second axis connecting the identified features of the patient's surrounding anatomy; measuring the angular difference between the first and second axes; and determining the axial rotation of the cervical vertebra based on the measurement. In some examples of the disclosure, determining the axial rotation of the cervical vertebra is based on the degree of perpendicularity between the first and second axes.

21 Claims, 5 Drawing Sheets

(58) Field of Classification Search
CPC ... G01R 33/34084; G01R 33/36; G01R 33/07
See application file for complete search history.

(56) References Cited

U.S. PATENT DOCUMENTS

| | | | |
|---|---|---|---|
| 4,411,270 A | 10/1983 | Damadian | |
| 4,534,076 A | 8/1985 | Barge | |
| 4,534,358 A | 8/1985 | Young | |
| D283,858 S | 5/1986 | Opsvik et al. | |
| 4,608,991 A | 9/1986 | Rollwitz | |
| 4,613,820 A | 9/1986 | Edelstein et al. | |
| 4,614,378 A | 9/1986 | Picou | |
| 4,629,989 A | 12/1986 | Riehl et al. | |
| 4,641,119 A | 2/1987 | Moore | |
| 4,651,099 A | 3/1987 | Vinegar et al. | |
| 4,663,592 A | 5/1987 | Yamaguchi et al. | |
| 4,664,275 A | 5/1987 | Kasai et al. | |
| 4,668,915 A | 5/1987 | Daubin et al. | |
| 4,672,346 A | 6/1987 | Miyamoto et al. | |
| 4,675,609 A | 6/1987 | Danby et al. | |
| 4,679,022 A | 7/1987 | Miyamoto et al. | |
| 4,707,663 A | 11/1987 | Minkoff et al. | |
| 4,766,378 A | 8/1988 | Danby et al. | |
| 4,767,160 A | 8/1988 | Mengshoel et al. | |
| 4,770,182 A | 9/1988 | Damadian et al. | |
| 4,777,464 A | 10/1988 | Takabatashi et al. | |
| 4,816,765 A | 3/1989 | Boskamp et al. | |
| 4,825,162 A | 4/1989 | Roemer et al. | |
| 4,829,252 A | 5/1989 | Kaufman | |
| 4,866,387 A | 9/1989 | Hyde et al. | |
| 4,875,485 A | 10/1989 | Matsutani | |
| 4,908,844 A | 3/1990 | Hasegawa et al. | |
| 4,918,388 A | 4/1990 | Mehdizadeh et al. | |
| 4,920,318 A | 4/1990 | Misic et al. | |
| 4,924,198 A | 5/1990 | Laskaris | |
| 4,943,774 A | 7/1990 | Breneman et al. | |
| 4,968,937 A | 11/1990 | Akgun | |
| 4,975,644 A | 12/1990 | Fox | |
| 4,985,678 A | 1/1991 | Gangarosa et al. | |
| 5,008,624 A | 4/1991 | Yoshida | |
| 5,030,915 A | 7/1991 | Boskamp et al. | |
| 5,050,605 A | 9/1991 | Eydelman et al. | |
| 5,061,897 A | 10/1991 | Danby et al. | |
| 5,062,415 A | 11/1991 | Weatherby et al. | |
| 5,065,701 A | 11/1991 | Punt | |
| 5,065,761 A | 11/1991 | Pell | |
| 5,081,665 A | 1/1992 | Kostich | |
| 5,124,651 A | 6/1992 | Danby et al. | |
| 5,134,374 A | 7/1992 | Breneman et al. | |
| 5,153,517 A | 10/1992 | Oppelt et al. | |
| 5,153,546 A | 10/1992 | Laskaris | |
| 5,155,758 A | 10/1992 | Vogl | |
| 5,162,768 A | 11/1992 | McDougall et al. | |
| 5,171,296 A | 12/1992 | Herman | |
| 5,194,810 A | 3/1993 | Breneman et al. | |
| 5,197,474 A | 3/1993 | Englund et al. | |
| 5,207,224 A | 5/1993 | Dickinson et al. | |
| 5,221,165 A | 6/1993 | Goszczynski | |
| 5,221,902 A | 6/1993 | Jones et al. | |
| 5,229,723 A | 7/1993 | Sakurai et al. | |
| 5,250,901 A | 10/1993 | Kaufman et al. | |
| 5,251,961 A | 10/1993 | Pass | |
| 5,256,971 A | 10/1993 | Boskamp | |
| 5,274,332 A | 12/1993 | Jaskolski et al. | |
| 5,291,890 A | 3/1994 | Cline et al. | |
| 5,304,932 A | 4/1994 | Carlson | |
| 5,305,365 A | 4/1994 | Coe | |
| 5,305,749 A | 4/1994 | Li et al. | |
| 5,305,750 A | 4/1994 | Makita | |
| 5,315,244 A | 5/1994 | Griebeler | |
| 5,315,276 A | 5/1994 | Huson et al. | |
| 5,317,297 A | 5/1994 | Kaufman et al. | |
| 5,323,113 A | 6/1994 | Cory et al. | |
| 5,349,956 A | 9/1994 | Bonutti | |
| 5,382,904 A | 1/1995 | Pissanetzky | |
| 5,382,905 A | 1/1995 | Miyata et al. | |
| 5,386,447 A | 1/1995 | Siczek | |
| 5,394,087 A | 2/1995 | Molyneaux | |
| 5,412,363 A | 5/1995 | Breneman et al. | |
| 5,436,607 A | 7/1995 | Chari et al. | |
| 5,471,142 A | 11/1995 | Wang et al. | |
| 5,473,251 A | 12/1995 | Mori | |
| 5,475,885 A | 12/1995 | Ishikawa et al. | |
| 5,477,146 A | 12/1995 | Jones | |
| 5,490,513 A | 2/1996 | Damadian et al. | |
| 5,515,863 A | 5/1996 | Damadian | |
| 5,519,372 A | 5/1996 | Palkovich et al. | |
| 5,548,218 A | 8/1996 | Lu | |
| 5,553,777 A | 9/1996 | Lampe | |
| 5,566,681 A | 10/1996 | Manwaring et al. | |
| 5,578,925 A | 11/1996 | Molyneaux et al. | |
| 5,592,090 A | 1/1997 | Pissanetzky | |
| 5,606,970 A | 3/1997 | Damadian | |
| 5,621,323 A | 4/1997 | Larsen | |
| 5,623,241 A | 4/1997 | Minkoff | |
| 5,640,958 A | 6/1997 | Bonutti | |
| 5,652,517 A | 7/1997 | Maki et al. | |
| 5,654,603 A | 8/1997 | Sung et al. | |
| 5,666,056 A | 9/1997 | Cuppen et al. | |
| 5,671,526 A | 9/1997 | Merlano et al. | |
| 5,680,861 A | 10/1997 | Rohling | |
| 5,682,098 A | 10/1997 | Vij | |
| 5,735,278 A | 4/1998 | Hoult et al. | |
| 5,743,264 A | 4/1998 | Bonutti | |
| 5,754,085 A | 5/1998 | Danby et al. | |
| 5,779,637 A | 7/1998 | Palkovich et al. | |
| 5,836,878 A | 11/1998 | Mock et al. | |
| 5,862,579 A | 1/1999 | Blumberg et al. | |
| 5,929,639 A | 7/1999 | Doty | |
| 5,951,474 A | 9/1999 | Matsunaga et al. | |
| D417,085 S | 11/1999 | Kanwetz, II | |
| 5,983,424 A | 11/1999 | Naslund et al. | |
| 5,988,173 A | 11/1999 | Scruggs | |
| 6,008,649 A | 12/1999 | Boskamp et al. | |
| 6,011,396 A | 1/2000 | Eckels et al. | |
| 6,014,070 A | 1/2000 | Danby et al. | |
| 6,023,165 A | 2/2000 | Damadian et al. | |
| 6,029,082 A | 2/2000 | Srinivasan et al. | |
| 6,075,364 A | 6/2000 | Damadian et al. | |
| 6,122,541 A | 9/2000 | Cosman et al. | |
| 6,137,291 A | 10/2000 | Szumowski et al. | |
| 6,138,302 A | 10/2000 | Sashin et al. | |
| 6,141,579 A | 10/2000 | Bonutti | |
| 6,144,204 A | 11/2000 | Sementchenko et al. | |
| 6,150,819 A | 11/2000 | Laskaris et al. | |
| 6,150,820 A | 11/2000 | Damadian et al. | |
| 6,201,394 B1 | 3/2001 | Danby et al. | |
| 6,208,144 B1 | 3/2001 | McGinley et al. | |
| 6,226,856 B1 | 5/2001 | Kazama et al. | |
| 6,246,239 B1 | 6/2001 | Krogmann et al. | |
| 6,246,900 B1 | 6/2001 | Cosman et al. | |
| 6,249,121 B1 | 6/2001 | Boskamp et al. | |
| 6,249,695 B1 | 6/2001 | Damadian | |
| 6,285,188 B1 | 9/2001 | Sakakura et al. | |
| 6,344,745 B1 * | 2/2002 | Reisker | G01R 33/34046 324/318 |
| 6,346,814 B1 | 2/2002 | Carrozzi et al. | |
| 6,357,066 B1 | 3/2002 | Pierce | |
| 6,369,571 B1 | 4/2002 | Damadian et al. | |
| 6,377,044 B1 | 4/2002 | Burl et al. | |
| 6,385,481 B2 | 5/2002 | Nose et al. | |
| 6,411,088 B1 | 6/2002 | Kuth et al. | |
| 6,414,490 B1 | 7/2002 | Damadian et al. | |
| 6,424,854 B2 | 7/2002 | Hayashi et al. | |
| 6,456,075 B1 | 9/2002 | Damadian et al. | |
| 6,504,371 B1 | 1/2003 | Damadian et al. | |
| 6,549,800 B1 | 4/2003 | Atalar et al. | |
| 6,591,128 B1 | 7/2003 | Wu et al. | |
| 6,608,917 B1 | 8/2003 | Wei et al. | |
| 6,639,406 B1 | 10/2003 | Boskamp et al. | |
| 6,656,143 B2 | 12/2003 | Browd | |
| 6,677,753 B1 | 1/2004 | Danby et al. | |
| 6,792,257 B2 | 9/2004 | Rabe et al. | |
| 6,801,038 B2 | 10/2004 | Carrozzi et al. | |

(56) References Cited

U.S. PATENT DOCUMENTS

| | | | |
|---|---|---|---|
| 6,806,711 | B2 | 10/2004 | Reykowski |
| 6,850,064 | B1 | 2/2005 | Srinivasan |
| 6,850,067 | B1 | 2/2005 | Burl et al. |
| 6,882,149 | B2 | 4/2005 | Nitz et al. |
| 6,882,877 | B2 | 4/2005 | Bonutti |
| 6,894,495 | B2 | 5/2005 | Kan |
| 6,954,069 | B2 | 10/2005 | Harvey et al. |
| 6,975,115 | B1 | 12/2005 | Fujita et al. |
| 6,980,002 | B1 | 12/2005 | Petropoulos et al. |
| 7,046,006 | B2 | 5/2006 | Creemers et al. |
| 7,049,819 | B2 | 5/2006 | Chan et al. |
| 7,123,008 | B1 | 10/2006 | Damadian et al. |
| 7,221,161 | B2 | 5/2007 | Fujita et al. |
| 7,245,127 | B2 | 7/2007 | Feng et al. |
| 7,348,778 | B2 | 3/2008 | Chu et al. |
| 7,450,985 | B2 | 11/2008 | Meloy |
| 7,474,098 | B2 | 1/2009 | King |
| 7,551,954 | B2 | 6/2009 | Green et al. |
| 7,680,525 | B1 | 3/2010 | Damadian et al. |
| 7,701,209 | B1 | 4/2010 | Green |
| 7,835,497 | B2 * | 11/2010 | Haras ............... A61B 5/1075 378/98 |
| 9,138,164 | B2 | 9/2015 | Driemel |
| 2001/0029330 | A1 | 10/2001 | Nose et al. |
| 2002/0013524 | A1 | 1/2002 | Hayashi et al. |
| 2002/0021128 | A1 | 2/2002 | Kuhara |
| 2002/0032927 | A1 | 3/2002 | Dinkier |
| 2002/0101241 | A1 | 8/2002 | Chui |
| 2002/0123681 | A1 | 9/2002 | Zuk et al. |
| 2002/0196021 | A1 | 12/2002 | Wang |
| 2003/0026469 | A1 | 2/2003 | Kreang-Arekul et al. |
| 2003/0059476 | A1 | 3/2003 | Wang |
| 2003/0210049 | A1 | 11/2003 | Boskamp et al. |
| 2003/0214301 | A1 | 11/2003 | Lee |
| 2005/0020945 | A1 | 1/2005 | Tosaya et al. |
| 2005/0122343 | A1 | 6/2005 | Bailey et al. |
| 2006/0051814 | A1 | 3/2006 | Jackowski et al. |
| 2007/0073195 | A1 | 3/2007 | Chen |
| 2010/0033183 | A1 | 2/2010 | Ochi et al. |
| 2011/0009749 | A1 | 1/2011 | Zamboni |
| 2011/0026801 | A1 | 2/2011 | Dohata et al. |
| 2011/0121833 | A1 * | 5/2011 | Sambandamurthy ....................... G01R 33/34084 324/318 |

FOREIGN PATENT DOCUMENTS

| | | |
|---|---|---|
| JP | 4-332531 | 11/1992 |
| JP | 62-26052 | 8/1994 |
| JP | 08-050843 A | 2/1996 |
| WO | 97/17896 | 5/1997 |

OTHER PUBLICATIONS

Hill et al. The role of adjustable scout lines in advanced spinal imaging. 2012 Proc. of the N.A.S.S. 27th annual meeting The Spine Journal 12 p.142S paper#P97.*

Karhu et al. Kinematic magnetic resonance imaging of the upper cervical spine using a novel positioning device. 1999 SPINE 24:2046-2056.*

Koller et al. Assessment of two measurement techniques of cervical spine and C1-C2 rotation in the outcome research of axis fractures 2010 SPINE 35:286-290.*

Salem et al. In vivo three-dimensional kinematics of the cervical spine during maximal axial rotation. 2013 Manual therapy 18:339-344.*

Kowalski et al. 1987 Am. J. NeuroRadiol. 8:697-702.*

Netto. 2006 BSc Thesis Mechanical Engineering, Edith Cowan University, Australia, 145 pages.*

Christensen 2005 American Journal of Physical Anthropology 127:291-295.*

Serrurier et al. 2005 ZAS Papers in Linguistics 40:195-211.*

Lam et al. 2008 Scoliosis 3 10 pages.*

Kouwenhoven et al. 2007 Spine 32:1123-1128.*

Prince and Links 2005 Medical Imaging Signals and Systems, Pearson and Prentica Hall, Chap. 13, MR imaging, p. 409-464.*

Takasaki et al. 2011 Manual Therapy 16:167-171 (Year: 2011).*

Kowalski et al. 1987 AJNR 8:697-702 (Year: 1987).*

Cakmakci 2009 Pediatr. Radiol. 39 (Suppl.3):S391-S405 (Year: 2009).*

Ishii et al. 2004a SPINE 29:E139-E144 (Year: 2004).*

Ishii et al. 2004b SPINE 29:2826-2831 (Year: 2004).*

Pfeuffer et al. 2004 Magnetic Resonance Imaging 22:1343-1359 (Year: 2004).*

Jinkins et al. 2002 Rivista di Neuroradiologia 15: 333-357 (Year: 2002).*

U.S. Appl. No. 14/209,279, filed Mar. 13, 2014.

U.S. Appl. No. 08/978,084, filed Nov. 25, 1997.

U.S. Appl. No. 10/131,843, filed Apr. 25, 2002.

U.S. Appl. No. 09/718,946, filed Nov. 22, 2000.

Weis et al., Simulation of the influence of magnetic field inhomogeneity and distortion correction in MR imaging, vol. 8, No. 4, p. 483-489, 1990 (Abstract).

"The design and construction of high field-uniformity permanent magnet system for MRI" Feng, Z.X.; Jiang, X.H.;Han, S.; Magnetics, IEEE Transactions on vol. 28, Issue 1, Jan. 1992 pp. 641-643.

Guclu et al., A method for Preamplifier-Decoupling Improvement in Quadrature Phased-Array Coils, Journal of Magnetic Resonance Imaging, 19:255-258, 2004.

Feng, et al., A New Phased Array Spine Coil for Vertical Field MRI System, Proc. Intl. Soc. Mag. Reson. Med. 11, 2003.

Three Dimensional Analysis of Spinal Deformities, M. D'Amico, et al., (Eds.), IOS Press, 1995, pp. 445-451.

Jinkins et al., Upright, Weight-bearing, Dynamic-kinetic Magnetic Resonance Imaging of the Spine—Review of the First Clinical Results, 2003, J HK Coll. Radiol., 6:55-74.

Ibell, The Design and Modelling of 2D Phases Arrays for MRI, Oct. 2003, Thesis, The University of Queensland.

Roemer, et al., The NMR Phases Array, Nov. 1990, Magenetic Resonance in Medicine 16, 192-225.

Bottomley et al., What is the Optimum Phased Array Coil Design for Cardiac and Torso Magnetic Resonance?, MRM 37:591-599, 1997.

Damadian et al., "The Possible Role of Cranio-Cervical Trauma and Abnormal CSF Hydrodynamics in the Generis of Multiple Sclerosis", Physiol. Chem. Phys. & Med. NMR (Sep. 20, 2011) 41:1-17.

Zamboni et al (CSF dynamics and brain volume in multiple sclerosis are associated with extracranial venous flow anomalies: a pilot program), Apr. 2010.

Hofmann et al (Phase-Contrast MR Imaging of the Cervical CSF and Spinal Cord: Volumetric Motion Analysis in Patients with Chiari I Malformation. AJNR Am J Neuroradial 21:151-158, Jan. 2000).

Batzdorf et al (Chiari malformation and syringomyelia, 2008).

Zamboni et al (Intracranial venous haemodynamics in multiple sclerosis, 2007).

Alperin et al., "Quantifying the effect of posture on intracranial physiology in humans by MRI flow studies", Journal of Magnetic Resonance Imaging 22:591-596 (2005).

* cited by examiner

CERVICAL VERTEBRA ANGLE MEASUREMENT

CROSS-REFERENCE TO RELATED APPLICATIONS

The present application claims the benefit of the filing date of U.S. Provisional Patent Application Nos. 61/779,165 and 61/779,388, both filed Mar. 13, 2013, the disclosures of which are hereby incorporated herein by reference in their entirety.

BACKGROUND

The present application relates to magnetic resonance imaging systems and methods for using such systems.

In magnetic resonance imaging, an object to be imaged as, for example, a body of a human subject is exposed to a strong, substantially constant static magnetic field. The static magnetic field causes the spin vectors of certain atomic nuclei within the body to randomly rotate or precess around an axis parallel to the direction of the static magnetic field. Radio frequency excitation energy is applied to the body, and this energy causes the nuclei to "precess" in phase and in an excited state. As the precessing atomic nuclei relax, weak radio frequency signals are emitted; such radio frequency signals are referred to herein as magnetic resonance signals.

Different tissues produce different signal characteristics. Furthermore, relaxation times are the dominant factor in determining signal characteristics. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase, amplitude, and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Despite the wide adoption of magnetic resonance imaging, X-ray detection continues to be the primary method used to detect certain abnormalities. One such abnormality is a rotation of a patient's cervical vertebra. Detecting and monitoring cervical vertebra rotation is important because such rotations can impact cerebral spinal fluid flow to and from the brain. If one of a patient's vertebrae is rotated improperly, it can significantly cut off flow of the cerebral spinal fluid, which can in turn create pressure buildup in the patient's brain. Monitoring a patient's cervical vertebra may require repeated exposure to x-rays. This repeated exposure, however, can cause damage to living tissue. It is, therefore, recommended that efforts to reduce exposure continue and that repeated X-ray exposure should be minimized.

MRI exams, by contrast, can be repeatedly done without health concerns, and can provide the same or better level of image detail as can X-ray imaging. In that regard, it is desirable to develop a method of detecting and monitoring cervical vertebra rotation using MRI.

With regard to the C1 and C2 (atlas and axis, respectively) cervical vertebrae, one difficulty in using MRI to monitor rotation of these two vertebrae is that they commonly lie on the boundary between head MRI scans (e.g., scans taken with a head coil) and cervical MRI scans (e.g., scans taken with a cervical belt coil). As such, neither the typical head or cervical MRI scan is adequate in diagnosing or monitoring these vertebrae. As such, it is desirable to generate an MRI image different from the typical head and back images normally generated for purposes of monitoring rotation of the C1 and C2 vertebrae.

SUMMARY

A method of measuring the axial rotation of a selected vertebra of a patient using a magnetic resonance (MR) image. The selected vertebra may be a cervical vertebra. The method may include: identifying, in the MR image, features of the selected vertebra; determining a first axis connecting the identified features of the vertebra; identifying, in the MR image, features of the patient's surrounding anatomy that are not the selected vertebra; determining a second axis connecting the identified surrounding anatomical features; measuring the angular difference between the first and second axes; and determining the axial rotation of the vertebra based on the measurement. In some examples of the disclosure, determining the axial rotation of the vertebra is based on the degree of perpendicularity between the first and second axes.

In some examples of the disclosure, the selected vertebra may be a C-2 vertebra and the MR image may show the C-2 vertebra along an axial plane of the patient. In such examples, the two or more features of the selected vertebra may include either anterior-most or posterior-most prominences of the cortical bone of the C-2 vertebra. Further, the surrounding anatomical features may include an anterior feature of the patient's anatomy, such as the nasal septum of the patient, and a relatively posterior feature of the patient's anatomy, such as the vertex of the uvula of the patient. These features may be visualized on an axial image of the cranio-cervical junction (foramen magnum, C1 and C2) and may extend along a sagittal plane of the patient. In some examples, the surrounding anatomical features may additionally or alternatively include a center of the axis of rotation of the C2 vertebra.

In other examples of the disclosure, the selected vertebra may be a C-1 vertebra and the MR image may show the C-1 vertebra along an axial plane of the patient. In such examples, the features of the selected vertebra may include the margins of the anterior-most or the posterior-most prominences of the cortical bone of the C-1 vertebra. Further, the surrounding anatomical features may include an anterior feature of the patient's anatomy, such as the nasal septum of the patient, and a relatively posterior feature of the patient's anatomy, such as the vertex of the uvula of the patient. Again, the features may be visualized on an axial image of the cranio-cervical junction (foramen magnum, C1 and C2) and may extend along a sagittal plane of the patient. In other examples, the surrounding anatomical features may additionally or alternatively include the dens center and/or spinal cord center of the patient.

The method may further include generating a scout MR image of the patient, the scout MR image showing a sagittal cross-section of the patient, and selecting an initial locating axis on the scout image. The initial locating axis defining an axial plane of the patient on which the selected vertebra is present or lies.

DETAILED DESCRIPTION

The present disclosure is generally directed to methods using magnetic resonance imaging (MRI) to measure an angular rotation of a selected cervical vertebra of the patient. Specifically discussed in the disclosure are methods for measuring the atlas and axis of the cervical vertebrae (hereinafter C1 and C2, respectively). However, it will be appreciated by those skilled in the art that the methods described herein may be similarly applied to other vertebrae of the patient.

In its most general form, measuring angular rotation of a cervical vertebra using an MR image involves the following steps: (a) identifying, in the MR image, two or more features of the selected vertebra, (b) determining a first axis connecting the identified features, (c) identifying, in the MR image, two or more features of the patient's anatomy, (d) determining a second axis that would connect the identified anatomical features, and (e) measuring the angular difference between the first and second axes. The axial rotation of the cervical vertebra is then determined based on the angle measurement of step (e). It should be understood that these steps of the operation do not have to be performed in the precise order presented above. Rather, various steps can be performed in a different order, or simultaneously. Moreover, steps may be added and/or omitted.

Figure 1:
FIG. 1 is a sagittal scout magnetic resonance (MR) image of a patient in accordance with a first embodiment of the present disclosure.
Figure 2:
FIG. 2 is another sagittal scout magnetic resonance (MR) image of a patient in accordance with a second embodiment of the present disclosure.

Initially, identifying features of a vertebra and its surrounding anatomy in an MR image necessarily requires that those features be captured in the MR image. Thus, before step (a) can be performed for a selected vertebra, one must first set the MRI apparatus up to capture an image of the patient that includes each of the to-be-identified vertebral and surrounding anatomical features of the patient. Setting up the MRI apparatus involves aligning the patient within the apparatus such that each of the to-be-identified anatomical features lies or is present in a common plane that is transverse to a slice-select magnetic field gradient of the apparatus. Aligning the patient in such a manner may be performed by first generating a scout MR image of the patient and determining whether each of the to-be-identified anatomical features lies within a single slice perpendicular of the scout image. In the case of aligning a patient to image one of the patient's cervical vertebrae, the scout MR image may be a sagittal cross-section of the patient. The sagittal scout image of FIG. 1, for instance, depicts several lines 1-24 representing substantially axial image slices of the patient. For further example, the sagittal scout image of FIG. 2 depicts several lines 1-22, again representing substantially axial images of a patient. In a situation where the to-be-identified anatomical features do not lie on a common line 1-24 (of FIG. 1) or 1-22 (of FIG. 2), the patient may be rotated, translated, or otherwise repositioned in the MRI system. Such repositioning is hereinafter termed aligning an axis of the patient, and may be performed in the manner described below and in concurrently filed and commonly owned U.S. application entitled "Method and Apparatus for Magnetic Resonance Imaging of the Cranio-Cervical Junction," the disclosure of which is hereby incorporated herein by reference in its entirety.

Figure 3:
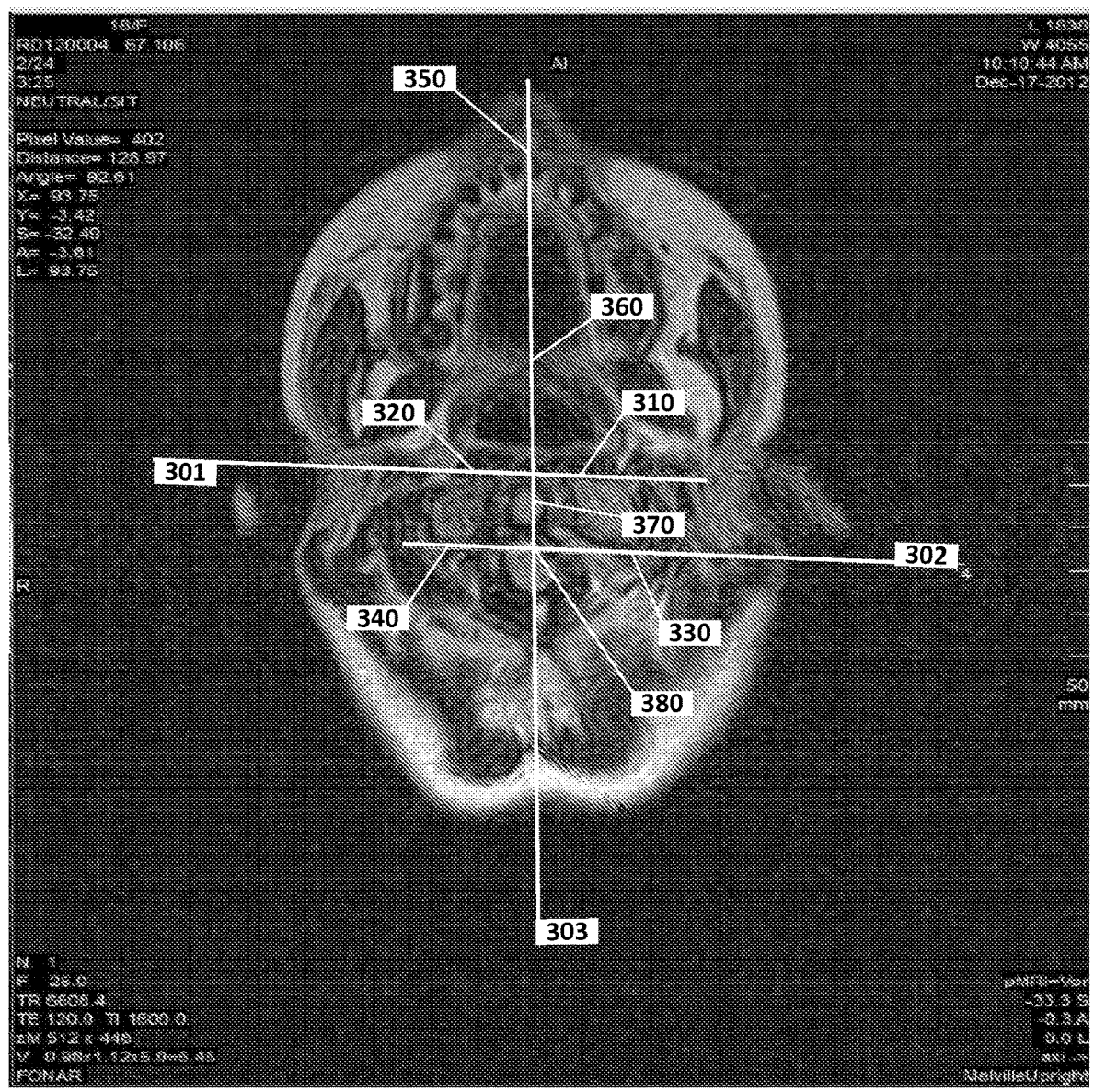
FIG. 3 is an axial MR image of a C1 vertebra in accordance with the first embodiment of the present disclosure.
Figure 4:
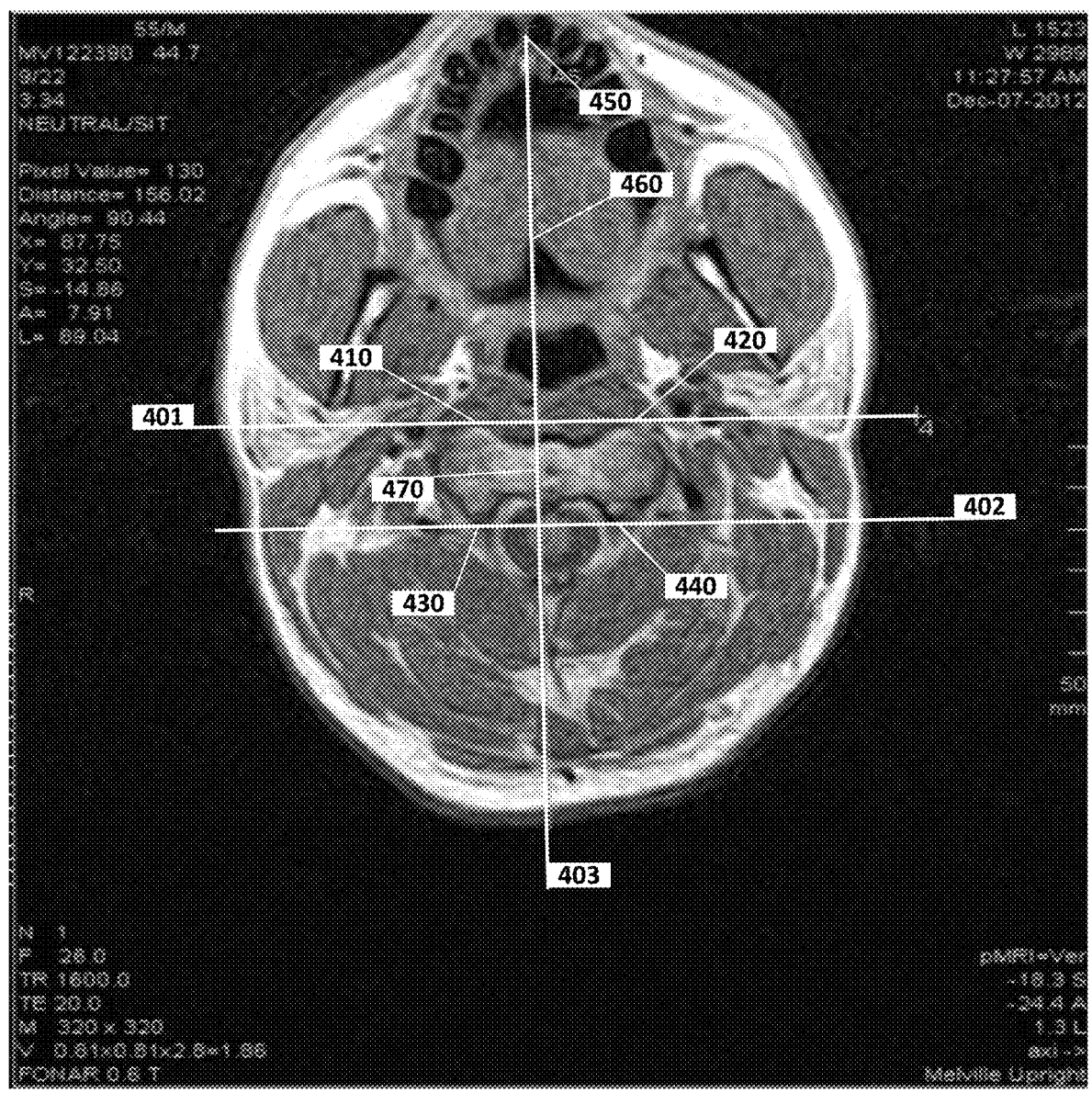
FIG. 4 is an axial MR image of a C2 vertebra in accordance with the second embodiment of the present disclosure.

Using the scout image, a particular transverse imaging plane of the patient having the selected vertebra (and the to-be-identified anatomical features) may be selected. Again, to illustrate, in the sagittal scout image of FIG. 1, for instance, the imaging plane represented by line 2 may be selected for measuring angular rotation of the C1 vertebra since that plane lines up with the C1 vertebra. This axial imaging plane is shown in FIG. 3. For further example, in the sagittal scout image of FIG. 2, the axial imaging plane represented by line 9 may be selected for measuring angular rotation of the C2 vertebra since that axial plane lines up with the mid-point of the C2 vertebra. This imaging plane is shown in FIG. 4.

Turning now to steps (a)-(e) of the method presented above, for purposes of clarity, these steps will be described in turn first as a method for measuring the angular rotation of a C1 vertebra (in the context of FIG. 3), and second as a method for measuring the angular rotation of a C2 vertebra (in the context of FIG. 4). As stated above, these descriptions are meant merely as examples of the more general process described above, which will be understood to similarly apply to other vertebrae of the patient.

Turning first to measuring the angular rotation of a C1 vertebra, in step (a), once an MR image along an axial plane of the C1 vertebra (FIG. 3, which is the image taken along line 2 of FIG. 1) has been acquired, features of the vertebra and of the patient's surrounding anatomy may be identified in the MR image. In one embodiment of the disclosure, the identified features of the C1 vertebra may be the cortical bone margins of the leftmost anterior lateral prominence (310), and the cortical bone margins of the rightmost anterior lateral prominence (320) respectively. Alternatively, the identified features of the C1 vertebra may be the most posterior cortical bone prominence (330) and the lateral cortical bone prominence (340).

In step (b), a first axis connecting the identified features of the C1 vertebra is determined. In the example of FIG. 3, if features 310 and 320 were indentified in step (a), then line 301, which is not actually part of the MR image but rather superimposed for illustration purposes, is the first axis on which the identified features lie. Alternatively, if features 330 and 340 were identified in step (a), then superimposed line 302 is the first axis on which the identified features lie.

In step (c), features of the patient's surrounding anatomy (i.e., that are not features of the C1 vertebra) are identified. In some examples (including the example of FIG. 3), at least one relatively anterior feature and at least one relatively posterior feature (i.e., relative to the anterior feature) of the patient's anatomy may be identified, such that the features lie or extend along a sagittal plane of the patient. In the example of the C1 vertebra of FIG. 3, such features may be the nasal septum of the patient (350), the vertex of the uvula midline (360), the dens center (370), and the spinal cord center (380).

In step (d), a second axis connecting the identified surrounding anatomical features is determined. In the example of FIG. 3, superimposed line 303 illustrates the axis on which the identified non-rotatable anatomical features 350, 360, 370, and 380 lie.

Lastly, in step (e), the angular difference between the first and second axes is measured. Essentially, the first axis represents the actual orientation the patient's vertebra, whereas the second axis represents the sagittal plane of the patient. Under normal circumstances, the first axis of a healthy patient should be perpendicular to the second axis, meaning that the patient's vertebra is in proper rotational alignment (e.g., relative to the surrounding anatomical features). However, when the first and second axes are not perpendicular, that is an indication that the vertebra of the patient is not properly rotationally aligned relative to the surrounding anatomical features.

In the example of the C1 vertebra, the axis represented by line 303 may be measured against the axis represented by either line 301 or line 302. Since lines 301 and 302 are parallel with one another, the result of measuring line 303 against either line 301 or 302 should be virtually the same. If line 303 lies substantially perpendicular to lines 301 and 302, then the C1 vertebra of the patient is properly rotationally aligned. However, if the measured angle between the measured lines 303 and 301/302 is not 90 degrees (e.g., 74 degrees, 106 degrees, etc.,), then the C1 vertebra is out of its rotational alignment, and the degree of the malalignment may be determined. The difference between the measured angle and 90 degrees can indicate the severity of the vertebral axial rotation.

The above method may be similarly applied to measuring the angular rotation of a C2 vertebra. In step (a), once an MR image along an axial plane of the C2 vertebra (FIG. 4, which is the image taken along line 9 of FIG. 2) has been acquired, features of the vertebra and the patient's surrounding anatomy may be identified in the MR image. In one embodiment of the disclosure, the identified features of the C2 vertebra may be the cortical bone on the most anterior prominences shown in the MR image (410 and 420). Alternatively, the identified features of the C2 vertebra may be the cortical bone of the posterior prominences shown in the MR image (430 and 440).

In step (b), a first axis connecting the identified features of the C2 vertebra is determined. If features 410 and 420 were identified in step (a), then superimposed line 401 is the first axis. Alternatively, if features 430 and 440 were identified, then superimposed line 402 is the first axis. It may be preferable to use the second axis when the anterior heights of most anterior prominences 410 and 420 are unequal. Likewise, it may be preferable to use the first axis when the most posterior prominences 430 and 440 are of unequal height. In circumstances when both the most anterior prominences 410 and 420 and most posterior prominences 430 and 440 are of unequal height, it may instead be preferable to define the first axis as the horizontal midline through the central hypointensity of the C2 vertebra between the lateral prominences.

In step (c), features of the patient's surrounding anatomy are identified, including, in some examples (including the example of FIG. 4), at least one anterior feature and at least one relatively posterior feature. In the example of the C2 vertebra of FIG. 4, such features may be the nasal septum (450) the vertex of the uvula (460), and the center of the axis of rotation of the C2 vertebra (470). It should be noted that the center point of the axis of rotation of the C2 vertebra 470, although technically a feature of the C2 vertebra, may still be used as a surrounding anatomical feature for purposes of this disclosure, since it lies on the second axis even when the C2 vertebra is rotated.

In step (d), a second axis connecting the identified non-rotatable anatomical features is determined. In the example of FIG. 4, superimposed line 403 illustrates the second axis on which the identified surrounding features 450, 460 and 470 lie.

Lastly, in step (e), the angular difference between the first and second axes is measured. This step is essentially the same as for the C1 measurement, described above. As with the C1 measurement, both lines 401 and 402 are substantially parallel, and as such, comparing either line against line 403 results in substantially the same measurement.

Figure 5:
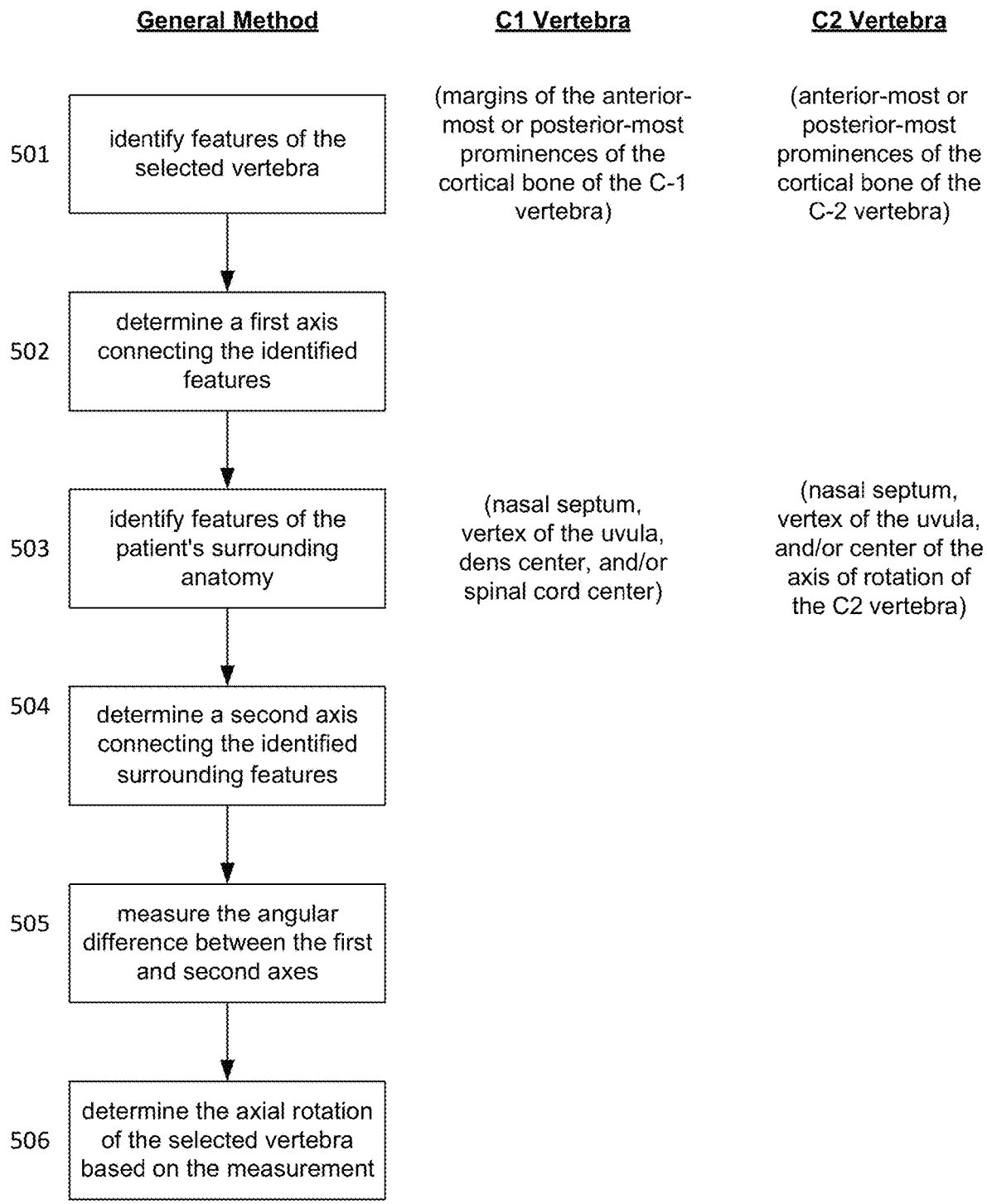
FIG. 5 illustrates a method according to another embodiment of the present disclosure.

FIG. 5 illustrates in a table format a summary of the general method described above and its application to axial rotation measurements of each the C1 and C2 vertebrae. The leftmost column of the table is illustrated as a flow chart having steps 501-506. Each of steps 501-505 generally corresponds to a respective step (a) through (e) of the above described method. In step 506, the axial rotation of the selected vertebra is determined based on the measurement of step 505. As described above, this determination is based on the degree of perpendicularity (or lack thereof) between the two measured axes. The middle and rightmost columns of the table summarize the specific application of the general steps 501-506 to each of the C1 and C2 measurements, respectively. Where application of a step is non-specific, the table is left blank.

The above described methods may be carried out using any MRI apparatus (e.g., bore-type, designs in which a patient is not upright, etc.), and preferably in any upright MRI apparatus, including the Fonar Upright® Multi-Position™ MRI. One such MRI apparatus having an MRI magnet subsystem and computing device for controlling the MRI magnet subsystem and generating images using the subsystem is described in greater detail in concurrently filed and commonly owned U.S. application Ser. No. 14/209,279 (now U.S. Pat. No. 9,766,310). The purpose of imaging a patient while upright is to gain a sense for the effect that gravity has on the vertebra of the patient. Moreover, a patient spends most of his or her time in an upright (standing or sitting) position. Thus although non-upright MRI systems and apparatuses may make use of the methods described herein, if the patient were imaged while lying down, the image may possibly not show the pressures (e.g., by gravity) or strains normally experienced by the vertebra of the patient. The upright apparatus may be positioned in a manner such that the patient is capable of standing or sitting on a pivoting base or platform (sometimes called a bed). The base may pivot forward or backward to change the orientation of the patient relative to the MRI magnet and/or imaging coils. In the method described above, the instruction provided to the bed to pivot, thereby reorienting the patient, is referred to as aligning an axis. The axis may be aligned by a user/operator of the apparatus by the user/operator viewing the anatomy of the patient on a screen and determining, based on the viewed image of the patient, whether (and how) the orientation of the patient should be changed, e.g., in order to place the anatomy of interest (i.e., a vertebra) in a single image slice or cross-section capable of being imaged by the apparatus.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of determining an impact to cerebral spinal fluid flow to and from a patient's brain based on a degree of axial rotational alignment between a selected CI or C2 vertebra of the patient's neck and the patient's surrounding anatomy, using an upright magnetic resonance imaging apparatus, the method comprising:
   (a) generating a magnetic resonance (MR) image of the patient in a standing or sitting position using a computing device and an imaging coil of the apparatus, wherein the imaging coil comprises:
      a saddle coil with anterior-posterior field sensitivity and having a length that permits for a center of the coil to reach the patient's cranial-cervical joint when slid over the patient's head: and
      a solenoid coil nested within the saddle element including a pair of rings, wherein a space between the pair of rings is adapted to position a highest signal-to-noise of the solenoid coil at the patient's cranial-cervical junction;
   (b) identifying, in the MR image, two or more features of the selected vertebra of the patient's neck,
   (c) determining a first axis connecting the identified features of the selected vertebra,
   (d) identifying, in the MR image, two or more features of the patient's surrounding anatomy that are not the selected vertebra,
   (e) determining a second axis connecting the identified features of the patient's surrounding anatomy, wherein the second axis represents a sagittal plane of the patient, measuring an angular difference between the first and second axes, wherein
   (f) the angular difference is indicative of an orientation of the selected vertebra relative to the sagittal plane of the patient, and
   (g) determining the degree of axial rotational alignment of the selected vertebra based on the measured angular difference.

2. The method of claim 1, wherein the selected vertebra is a C-2 vertebra and the MR image shows the C-2 vertebra along an axial plane of the patient.

3. The method of claim 2, wherein the two or more features of the selected vertebra comprise anterior-most prominences of the cortical bone of the C-2 vertebra.

4. The method of claim 2, wherein the two or more features of the selected vertebra comprise posterior-most prominences of the cortical bone of the C2 vertebra.

5. The method of claim 2, wherein the second axis extends along a sagittal plane of the patient.

6. The method of claim 2, wherein the two or more features of the patient's surrounding anatomy comprise at least one of the nasal septum of the patient and the vertex of the uvula of the patient.

7. The method of claim 2, wherein the two or more features of the patient's surrounding anatomy comprise a center of the axis of rotation of the C2 vertebra.

8. The method of claim 1, wherein the selected vertebra is a C-1 vertebra and the MR image shows the C-1 vertebra along an axial plane of the patient.

9. The method of claim 8, wherein the two or more features of the selected vertebra comprise the margins of the anterior-most prominences of the cortical bone of the C-1 vertebra.

10. The method of the claim 8, wherein the two or more features of the selected vertebra comprise the margins of the posterior-most prominences of the cortical bone of the C-1 vertebra.

11. The method of claim 8, wherein the second axis extends along the sagittal plane of the patient.

12. The method of claim 8, wherein the two or more features of the patient's surrounding anatomy comprise at least one of the nasal septum of the patient and the vertex of the uvula of the patient.

13. The method of claim 8, wherein the two or more features of the patient's surrounding anatomy comprise the dens center of the patient.

14. The method of claim 8, wherein the two or more features of the patient's surrounding anatomy comprise the spinal cord center of the patient.

15. The method of claim 1, wherein determining the degree of axial rotational alignment of the selected vertebra is based on the degree of perpendicularity between the first and second axes.

16. The method of claim 1, further comprising:
   generating a MRI of the patient, the MRI showing a sagittal cross-section of the patient; and
   selecting an initial locating axis on the image, the initial locating axis defining an axial plane of the patient on which the selected vertebra lies.

17. The method of claim 1, wherein a difference between (i) 90 degrees and (ii) the angular difference between the first and second axes is indicative of a degree of severity of an axial rotational malalignment.

18. The method of claim 1, further comprising:
   generating a scout MR image of the patient using a computing device and the apparatus; and
   selecting a line across the scout MR image intersecting each of the selected vertebra and the surrounding anatomical features,
   wherein the MR image of the patient is generated at a plane parallel with the selected line.

19. The method of claim 1, wherein each of the two or more features of the patient's surrounding anatomy is not included in any of the vertebra of the patient's spine.

20. The method of claim 1, wherein the imaging coil is positioned between a head coil position and a cervical belt coil position.

21. The method of claim 20, wherein the imaging coil has a magnetic field sensitivity oriented to be used within the upright magnetic resonance imaging apparatus.

* * * * *